US006682722B2

(12) United States Patent
Majeti et al.

(10) Patent No.: US 6,682,722 B2
(45) Date of Patent: Jan. 27, 2004

(54) ORAL COMPOSITIONS PROVIDING ENHANCED OVERALL CLEANING

(75) Inventors: Satyanarayana Majeti, Cincinnati, OH (US); Niteen Vasant Bapat, Cincinnati, OH (US); Paula Denise Clymer, Mason, OH (US); Elizabeth Ann Reno, Fairfield, OH (US); William Michael Glandorf, Mason, OH (US); Stephen Andras Kovacs, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/233,880

(22) Filed: Sep. 3, 2002

(65) Prior Publication Data

US 2003/0124065 A1 Jul. 3, 2003

Related U.S. Application Data

(60) Provisional application No. 60/323,304, filed on Sep. 19, 2001.

(51) Int. Cl.$^7$ ............................. A61K 7/16; A61K 7/20
(52) U.S. Cl. ............................................ 424/53; 424/49
(58) Field of Search ..................... 424/49–85

(56) References Cited

U.S. PATENT DOCUMENTS

| | | |
|---|---|---|
| 3,678,154 A | 7/1972 | Widder et al. |
| 3,737,522 A | 6/1973 | Francis et al. |
| 4,138,477 A | 2/1979 | Gaffar |
| 4,627,977 A | 12/1986 | Gaffar et al. |
| 4,661,341 A | 4/1987 | Benedict et al. |
| 4,775,525 A | 10/1988 | Pera |
| 4,847,070 A | 7/1989 | Pyrz et al. |
| 4,923,684 A | 5/1990 | Ibrahim et al. |
| 5,015,467 A | 5/1991 | Smitherman |
| 5,096,701 A | 3/1992 | White, Jr. et al. |
| 5,176,900 A | 1/1993 | White, Jr. et al. |
| 5,338,537 A | 8/1994 | White, Jr. et al. |
| 5,451,401 A | 9/1995 | Zerby et al. |
| 5,538,714 A | 7/1996 | Pink et al. |
| 5,622,689 A | 4/1997 | Lukacovic |
| 5,670,138 A | 9/1997 | Venema et al. |
| 5,849,271 A | 12/1998 | Lukacovic |
| 6,475,469 B1 | 11/2002 | Montgomery |

FOREIGN PATENT DOCUMENTS

| | | |
|---|---|---|
| DE | 490384 | 8/1938 |
| EP | 0 172 671 A2 | 2/1996 |
| EP | 0 979 649 A2 | 8/1999 |
| GB | 741315 | 11/1955 |
| GB | 2200551 A | 8/1988 |
| JP | 2000063250 | 8/1998 |
| JP | 2000-063250 A | 2/2000 |
| WO | WO 99/12517 A1 | 3/1999 |
| WO | WO 01/68045 A1 | 9/2001 |

Primary Examiner—Shep K. Rose
(74) Attorney, Agent, or Firm—Emelyn DeLeon Hiland

(57) ABSTRACT

Disclosed are oral care compositions and methods for overall cleaning, whitening and preventing, reducing or removing surface deposited stains on natural teeth and dental prosthesis, the compositions comprising in an orally acceptable carrier at least 0.1% by weight of a water-soluble or water-dispersible copolymer prepared by copolymerizing one or a mixture of vinyl pyrrolidone (VP) monomers with one or a mixture of C1–C19 alkyl carboxylic acid (AC) C2–C12 alkenyl ester monomers. Preferably, the compositions further comprise one or a mixture of other oral care agents selected from a water soluble alkali metal or ammonium tripolyphosphate in an amount at least about 0.5% by weight of the composition, an abrasive, preferably a precipitated silica abrasive, in an amount at least about 6% by weight of the composition and a bleaching agent in an amount at least about 0.1% by weight of the composition. This invention further relates to methods of cleaning, whitening and polishing natural teeth and dental prosthesis and of preventing, reducing or removing surface deposited stains from teeth by administering the present compositions.

17 Claims, No Drawings

ORAL COMPOSITIONS PROVIDING ENHANCED OVERALL CLEANING

CROSS REFERENCE TO RELATED APPLICATIONS

This application claims the benefit under 35 USC 119(e) to U.S. Application Serial No. 60/323,304 filed Sep. 19, 2001.

FIELD OF THE INVENTION

Disclosed are oral compositions and methods for enhanced overall cleaning, whitening, stain removal and preventing of staining of natural teeth and dental prosthesis. In particular, these benefits are achieved by applying to the teeth compositions comprising in an orally acceptable carrier a copolymer comprised of vinyl pyrrolidone (VP) and alkenyl carboxylate (AC) monomers.

BACKGROUND OF THE INVENTION

The formation of dental plaque and calculus is the primary source of dental caries, gingivitis, periodontal disease, and tooth loss. Dental plaque is a mixed matrix of bacteria, epithelial cells, leukocytes, macrophages and other oral exudate. Bacteria comprise approximately three-quarters of the plaque matrix. Any given sample of dental plaque could contain as many as 400 different varieties of microorganisms. This mix includes both aerobic and anaerobic bacteria, fungi, and protozoa. Viruses have also been found in samples of dental plaque.

This matrix of organisms and oral exudate continues expanding and coalesces with other plaque growths situated nearby. The bacteria synthesize levans and glucans from sucrose found in the oral cavity providing energy for the microorganisms. These glucans, levans, and microorganisms form an adhesive skeleton for the continued proliferation of plaque.

Dental calculus, or tartar as it is sometimes called, is a deposit which forms on the surfaces of the teeth at the gingival margin. Supragingival calculus appears principally in the areas near the orifices of the salivary ducts; e.g., on the lingual surfaces of the lower anterior teeth and on the buccal surfaces of the upper first and second molars, and on the distal surfaces of the posterior molars. Mature calculus consists of an inorganic portion which is largely calcium phosphate arranged in a hydroxyapatite crystal lattice structure similar to bone, enamel and dentine. An organic portion is also present and consists of desquamated epithelial cells, leukocytes, salivary sediment, food debris and various types of unless stained or discolored by some extraneous agent. In addition to being unsightly and undesirable from an aesthetic standpoint, the mature calculus deposits are constant sources of irritation of the gingiva.

The failure to retard or stop the proliferation of plaque and calculus is detrimental to oral health. Plaque and calculus formation may lead to dental caries, gingival inflammation, periodontal disease, and ultimately tooth loss. Additionally, calculus and plaque along with behavioral and environmental factors lead to formation of dental stains, significantly affecting the aesthetic appearance of teeth. Behavioral and environmental factors that contribute to teeth staining propensity include regular use of coffee, tea, cola or tobacco products, and also the use of stain promoting oral products, such as chlorhexidine.

The ultimate oral cleaning level is what dentists provide during prophylaxis; daily oral care at home requires products with multiple ingredients working by different mechanisms to provide satisfactory cleaning and whitening. Thus, for oral care products for daily use such as dentifrice and rinses to provide overall cleaning, it is necessary to add ingredients for provision of antiplaque and anticalculus benefits as well as stain removal, stain control and tooth whitening. Such ingredients for removal and control of stain and for whitening include bleaches, abrasives or chemical chelants. Bleaches added to dentifrices are typically present in low concentrations due to stability and safety limits unique to toothpastes. At these low concentrations, bleaches which are typically oxidizing agents, are generally ineffective at tooth whitening and stain control. Dental abrasives provide important whitening benefits, particularly on 'brushed' areas of teeth, but unfortunately are of limited effect in controlling aesthetically undesirable stains that form along the gumline and interproximally. Bleaches and abrasives do not functionally act to prevent acquisition of stains. Abrasive use can reduce rates of stain acquisition by daily removal of newly acquired stains, but this action is a 'treatment' for existing stain, not a preventive chemical action.

Chemical chelants have been suggested in the art to retard calculus formation and to remove calculus after it is formed. The chemical approach to calculus inhibition generally involves chelation of calcium ion and/or crystal growth inhibition which prevents the calculus from forming and/or breaks down mature calculus by removing calcium. In addition, chemical chelants can in principle remove stains by binding to teeth surfaces thereby displacing color bodies or chromagens. The retention of these chelants can also prevent stains from accruing due to disruption of binding sites of color bodies on tooth surfaces.

A number of agents with chelating properties for use in controlling plaque, calculus and stain have been disclosed in the art. For example, ethylenediaminetetraacetic acid, nitrilotriacetic acid and related compounds are disclosed in British Patent 490,384, Feb. 15, 1937; polyphosphonates in U.S. Pat. No. 3,678,154, Jul. 18, 1972 to Widder et al., U.S. Pat. No. 5,338,537 issued to Aug. 16, 1994 to White, Jr., and U.S. Pat. No. 5,451,401 issued Sep. 19, 1995 to Zerby et al.; carbonyl diphosphonates in U.S. Pat. No. 3,737,533, Jun. 5, 1973 to Francis; a zinc-polymer combination formed by the reaction or interaction of a zinc compound with an anionic polymer containing carboxylic, sulfonic and/or phosphonic acid radicals in U.S. Pat. No. 4,138,477, issued Feb. 6, 1979, to Gaffar; tartaric acid in U.S. Pat. No. 5,849,271 issued Dec. 15, 1998 and U.S. Pat. No. 5,622,689 issued Apr. 22, 1997 both to Lukacovic; acid or salt form of tartrate monosuccinate, tartrate disuccinate, and mixtures thereof in U.S. Pat. No. 5,015,467 issued May 14, 1991 to Smitherman; acrylic acid polymer or copolymer in U.S. Pat. No. 4,847,070, Jul. 11, 1989 to Pyrz et al. and in U.S. Pat. No. 4,661,341, Apr. 28, 1987 to Benedict et al.; sodium alginate in U.S. Pat. No. 4,775,525, issued Oct. 4, 1988, to Pera; polyvinyl pyrrolidone in GB 741,315 published Nov. 30, 1955, WO 99/12517 published Mar. 18, 1999 and U.S. Pat. No. 5,538,714 issued Jul. 23, 1996 to Pink et al.; and copolymers of vinyl pyrrolidone with carboxylates in U.S. Pat. No. 5,670,138 issued Sep. 23, 1997 to Venema et al. and in JP Publication No. 2000-0633250 to Lion Corporation, published Feb. 29, 2000.

Dentifrices and mouthwashes containing soluble pyrophosphate salts have also been disclosed in the art, the pyrophosphates being indicated for a variety of purposes including as anticalculus agent. Included among such disclosures are U.S. Pat. No. 2,941,926, Jun. 21, 1960 to Salzmann et al.; U.S. Pat. Nos. 3,927,201 and 3,927,202, Dec. 16, 1975 to Baines et al. and Harvey et al., respectively; U.S. Pat. No. 4,244,931, Jan. 13, 1981 and U.S. Pat. No. 4,247,526, Jan. 27, 1981 to Jarvis et al.; Japanese Patent Application No. 4945-1974; U.S. Pat. No. 4,323,551 issued Apr. 6, 1982, U.S. Pat. No. 4,515,772 issued May 7, 1986 and U.S. Pat. No. 4,885,155 issued Dec. 5, 1989 to Parran et al.; and U.S. Pat. No. 4,822,599 issued Apr. 18, 1989 to Mitra. Also Draus, Lesniewski and Miklos disclose the in vitro effectiveness of soluble pyrophosphate salts against calculus in "Pyrophosphate and Hexametaphosphate Effects in Vitro Calculus Formation", *Arch. Oral Biol.*, Vol. 15, pp. 893–896, (1970).

Linear molecularly dehydrated polyphosphate salts for use as calculus inhibitor are disclosed in U.K. Patent Application GB 2,200,551, Gaffar, Nabi and Jannone, filed Jan. 27, 1988, published Aug. 10, 1988; and in U.S. Pat. No. 4,627,977, issued Dec. 9, 1986, to Gaffar et al. Included among the salts is sodium tripolyphosphate (STPP). Other references disclosing STPP include U.S. Pat. No. 4,923,684, May 8, 1990 to Ibrahim et al. and U.S. Pat. No. 5,096,701 issued Mar. 17, 1992 and U.S. Pat. No. 5,176,900 issued Jan. 5, 1993 both to White et al.

Although products containing chemical chelants and other plaque and calculus reduction agents are known, there is a continuing need to develop improved products, in particular products that provide enhanced overall cleaning by concurrently attacking the calculus, plaque, and staining problems.

The present inventors have discovered that administration of oral compositions containing particular water-soluble or water-dispersible polymeric agents that bind color bodies such as polyphenols or catechols provides enhanced cleaning, stain removal and whitening of teeth. Additionally, the present polymeric agents when combined with polyphosphates, particularly tripolyphosphates, with abrasives, particularly precipitated silica or with bleaching agents, provide overall cleaning and whitening beyond that provided by any one of the ingredients alone. The present invention therefore provides oral compositions comprising specific water-soluble or water-dispersible polymeric agents that bind color bodies present in the oral cavity and a method of administering said oral compositions to provide enhanced overall cleaning, stain removal, stain prevention and whitening of teeth. Preferably, the present compositions further comprise one or a mixture of other oral care agents selected from a tripolyphosphate salt, an abrasive and a bleaching agent to provide even better cleaning performance as a result of synergy between the polymeric complexing agent and the other oral care agent.

SUMMARY OF THE INVENTION

The present invention provides oral compositions for overall cleaning and whitening of natural teeth and dental prosthesis and for preventing, reducing or removing of surface deposited stains on teeth, the compositions comprising at least 0.1% by weight of a copolymer comprised of one or a mixture of vinyl pyrrolidone (VP) monomers and one or a mixture of C2–C12 alkenyl C1–C19 alkyl carboxylate (AC) monomers and an orally acceptable carrier. Preferably, the compositions further comprise one or a mixture of other oral care agents selected from a water soluble alkali metal or ammonium tripolyphosphate in an amount at least about 0.5% by weight of the composition, an abrasive, preferably a precipitated silica abrasive, in an amount at least about 6% by weight and a bleaching agent in an amount at least about 0.1% by weight. This invention further relates to methods of cleaning, whitening and polishing natural teeth and dental prosthesis and of preventing, reducing or removing surface deposited stains from teeth by administering the present compositions.

These and other features, aspects, and advantages of the present invention will become evident to those skilled in the art from the detailed description which follows.

DETAILED DESCRIPTION OF THE INVENTION

While the specification concludes with claims which particularly point out and distinctly claim the invention, it is believed the present invention will be better understood from the following description.

All documents cited are, in relevant part, incorporated herein by reference; the citation of any document is not to be construed as an admission that it is prior art with respect to the present invention.

All percentages and ratios used herein are by weight of the specific oral composition and not of the overall oral formulation that is delivered, unless otherwise specified. All measurements are made at 25° C., unless otherwise specified.

Herein, "comprising" means that other steps and other ingredients which do not affect the end result can be added. This term encompasses the terms "consisting of" and "consisting essentially of".

By "oral composition" is meant a product which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral composition of the present invention may be in the form of a toothpaste, dentifrice, tooth powder, topical oral gel, mouthrinse, denture product, mouthspray, lozenge, oral tablet, or chewing gum.

The term "dentifrice", as used herein, means paste, gel, or liquid formulations unless otherwise specified. The dentifrice composition may be a single phase composition or may be a combination of two or more dentifrice compositions. The dentifrice composition may be in any desired form, such as deep striped, surface striped, multilayered, having the gel surrounding the paste, or any combination thereof. Each dentifrice composition in a dentifrice comprising two or more separate dentifrice compositions may be contained in a physically separated compartment of a dispenser and dispensed side-by-side.

The term "dispenser", as used herein, means any pump, tube, or container suitable for dispensing toothpaste.

The term "teeth", as used herein, refers to natural teeth as well as artificial teeth or dental prosthesis.

The term "orally acceptable carrier" as used herein means any safe and effective materials for use in the compositions of the present invention. Such materials include fluoride ion sources, additional anticalculus agents, buffers, abrasive polishing materials, peroxide sources, alkali metal bicarbonate salts, thickening materials, humectants, water, surfactants, titanium dioxide, flavor system, sweetening agents, xylitol, coloring agents, and mixtures thereof.

Herein, the terms "tartar" and "calculus" are used interchangeably and refer to mineralized dental plaque deposits.

The present invention provides oral compositions that provide enhanced overall cleaning and whitening of and stain removal from teeth, the compositions comprising as an essential ingredient one or more water-soluble or water-dispersible polymeric agents that are capable of binding color bodies such as polyphenols. In particular, the water-soluble or water-dispersible polymeric agents are copolymers prepared by copolymerizing one or a mixture of vinyl pyrrolidone (VP) monomers with one or a mixture of alkenyl carboxylate (AC) monomers, specifically C2–C12 alkenyl esters of saturated straight- or branched-chain C1–C19 alkyl carboxylic acids, as follows:

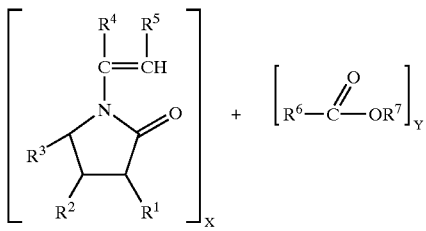

wherein $R^1$, $R^2$, $R^3$, $R^4$, $R^5$=H or saturated C1–C12 alkyl,
$R^6$=saturated C1–C19 alkyl,
$R^7$=C2–C12 monoalkenyl, and
the x/y ratio ranges from about 30/70 to about 90/10.

Preferred ester monomers include the vinyl, allyl and methallyl esters of linear or branched aliphatic carboxylic acids having 2 to 20 carbons, such as vinyl acetate, propionate, butyrate, valerate, hexanoate, 2-ethylhexanoate, decanoate, laurate and stearate, and the corresponding allyl and methallyl esters. Preferred vinyl pyrrolidone monomer is unsubstituted. Particularly preferred polymers include copolymers of vinyl pyrrolidone with one or a mixture of vinyl acetate, vinyl propionate, or vinyl butyrate. Preferred polymers have an average molecular weight ranging from about 1,000 to about 1,000,000, preferably from 10,000 to 200,000, even more preferably from 30,000 to 100,000. The present copolymers are generally prepared by free-radical solution or emulsion polymerization using solvents such as water, aliphatic alcohols of 1 to 4 carbons, or in alcohol/water mixtures, as described for example, in U.S. Pat. Nos. 2,667,473; 4,520,179; 4,554,311; 5,319,041; 5,395,904; 6,107,397; and 6,103,820.

Preferably, the compositions further comprise at least about 0.5% by weight of a water soluble tripolyphosphate salt and/or at least about 6% by weight of an abrasive polishing agent, such as silica and/or at least about 0.1% of a bleaching agent.

The present inventors have discovered that the cleaning and whitening properties of vinyl pyrrolidone (VP) polymers can be greatly enhanced by changing their water solubility and hydrophobicity. One way to increase the hydrophobicity is to copolymerize vinyl pyrrolidones with a series of hydrophobic alkenyl carboxylates. The resulting copolymers not only possess the polar pyrrolidone amide bonds and the carboxylate ester groupings, but also contain hydrophobic alkyl functionalities to provide greater retention on teeth and superior stain removal and prevention.

Without wishing to be limited to a particular mechanism of action, it is believed that the superior stain removal and prevention benefits of the present copolymers are derived at least in part from their ability to form complexes with color bodies such as polyphenolic compounds and from their ability to form a coating or film on tooth surfaces. Polyphenols, also called catechols and tannins, are constituents of various dietary products such as tea, coffee, wine, cola, and a variety of fruits and berries. Consumption of these dietary products are known to cause deposition of staining materials on teeth. It is believed that the present PVP/AC copolymers form a protective film on the tooth surface when the present compositions are applied to the oral cavity such as by toothbrushing or by rinsing. Thus when color bodies are present in the oral cavity, they contact the PVP/AC film coating instead of the tooth surface and form a complex with the PVP/AC copolymer. The PVP/AC/color body complex then gets lifted away from the tooth surface as the transient PVP/AC film sloughs off the surface, thereby preventing stain from forming on the teeth. With regard to the stain removal aspect, the copolymer is believed to be functioning in conjunction with other cleaning agents in the product such as abrasives, surfactants and chelating agents. The action of these agents causes the already existing stain on teeth to come off the surface and the copolymer forms a complex with the released color bodies and prevents their redeposition on the teeth. In this regard, the function of the copolymer is synergistic with the other cleaning ingredients. Freshly formed plaque can also be prevented from its formation on teeth and the copolymer inhibits the ability of plaque to absorb colored components from ingested products such as tea, beer, red wines, etc.

A suitable copolymer for use in the present invention is a vinyl pyrrolidone/vinyl acetate copolymer (PVP/VA) having 60/40 weight ratio of VP/VA and an average molecular weight ranging from about 1,000 to about 1,000,000 available from BASF Corp. and ISP. Preferred polymers are those with an average molecular weight ranging from 30,000 to 100,000. Copolymers having a VP/VA ratio ranging from 30/70 to 90/10 are also suitable. The copolymer is incorporated in the present compositions at about 0.1% to about 20% by weight and preferably from about 0.5% to about 10% by weight.

Preferably, the present compositions further comprise a water-soluble alkali metal or ammonium tripolyphosphate salt. The sodium form of this salt is preferred, although the potassium salt or mixed sodium and potassium salts may also be used. This tripolyphosphate salt is supplied as a hydrate or in its dehydrated form from Monsanto Corp. or Sigma Chemical; and both forms are suitable for use in the compositons. The amount of tripolyphosphate salt will be at least about 0.5% by weight up to about 50%. The practical limit to the amount of tripolyphosphate salt is mainly solubility. A preferred amount of tripolyphosphate salt is from about 2% to about 20% by weight in dentifrice formulations.

While the present copolymer is active in its own right as a stain control agent, it has been surprisingly found that the combination of the copolymer with a tripolyphosphate salt provides a synergistic benefit in removing and preventing stains, far in excess of either agent alone.

The present compositions preferably also comprise at least about 6% of a polishing agent or abrasive, preferably a silica abrasive. The present inventors have discovered that the combination of the copolymer with an abrasive polishing agent provides significantly enhanced polishing benefits to tooth enamel surfaces, in addition to cleaning and stain removal. The polishing benefits include improved teeth appearance as well as positive tooth feel characteristics.

The present compositions preferably further comprise a teeth whitening agent, such as a bleach, a peroxide in particular. The present copolymers have been found to form complexes with inorganic compounds especially with hydrogen peroxide. Thus, the present copolymers provide a stabilizing benefit to the peroxide component when present in the compositions herein.

Accordingly, in one aspect of the invention, there is provided a composition for use in whitening and cleaning teeth and dental prosthesis comprising a copolymer of vinyl pyrrolidone (VP) with an alkenyl carboxylate (AC). In a further aspect, there is provided a composition comprising the combination of a VP/AC copolymer and from about 0.1% to about 20.0% bleaching agent, more preferably from about 1% to about 15% bleaching agent. In another aspect of this invention, there is provided a composition for use in cleaning, whitening, removing stain and preventing stain build-up on teeth and dental prosthesis comprising a combination of a water-soluble alkali metal or ammonium tripolyphosphate salt and a VP/AC copolymer. In still another aspect, there is provided a composition additionally providing enhanced polishing benefits, comprising a VP/AC copolymer and an abrasive agent.

The oral composition of the present invention may be in the form of a dentifrice, toothpaste, tooth powder, topical oral gel, mouthrinse, denture product, mouthspray, lozenge, oral tablet, or chewing gum.

The present compositions will optimally have a pH ranging from about 4.0 to about 10.0 Preferred pH of the compositions is from about 6.0 to about 9.0.

In addition to the components described above, the present compositions may comprise additional components, which are described in the following paragraphs.

Orally Acceptable Carrier

The orally acceptable carrier comprises one or more compatible solid or liquid filler diluents or encapsulating substances which are suitable for topical oral administration. By "compatible," as used herein, is meant that the components of the composition are capable of being commingled without interaction in a manner which would substantially reduce the composition's stability and/or efficacy.

The carriers or excipients of the present invention can include the usual and conventional components of dentifrices (including non-abrasive gels and gels for subgingival application), mouth rinses, mouth sprays, chewing gums, and lozenges (including breath mints) as more fully described hereinafter.

The choice of a carrier to be used is basically determined by the way the composition is to be introduced into the oral cavity. If a toothpaste (including tooth gels, etc.) is to be used, then a "toothpaste carrier" is chosen (e.g., abrasive materials, sudsing agents, binders, humectants, flavoring and sweetening agents, etc.) as disclosed in, e.g., U.S. Pat. No. 3,988,433, to Benedict. If a mouth rinse is to be used, then a "mouth rinse carrier" is chosen (e.g., water, flavoring and sweetening agents, etc.), as disclosed in, e.g., U.S. Pat. No. 3,988,433 to Benedict. Similarly, if a mouth spray is to be used, then a "mouth spray carrier" is chosen or if a lozenge is to be used, then a "lozenge carrier" is chosen (e.g., a candy base), candy bases being disclosed in, e.g., U.S. Pat. No. 4,083,955, to Grabenstetter et al.; if a chewing gum is to be used, then a "chewing gum carrier" is chosen (e.g., gum base, flavoring and sweetening agents), as disclosed in, e.g., U.S. Pat. No. 4,083,955, to Grabenstetter et al. If a sachet is to be used, then a "sachet carrier" is chosen (e.g., sachet bag, flavoring and sweetening agents). If a subgingival gel is to be used (for delivery of actives into the periodontal pockets or around the periodontal pockets), then a "subgingival gel carrier" is chosen as disclosed in, e.g. U.S. Pat. Nos. 5,198,220 and 5,242,910, issued Mar. 30, 1993 and Sept. 7, 1993, respectively both to Damani. Carriers suitable for the preparation of compositions of the present invention are well known in the art. Their selection will depend on secondary considerations like taste, cost, and shelf stability, etc.

The compositions of the present invention may be in the form of non-abrasive gels, including subgingival gels, which may be aqueous or non-aqueous. Aqueous gels generally include a thickening agent (from about 0.1% to about 20%), a humectant (from about 10% to about 55%), a flavoring agent (from about 0.04% to about 2%), a sweetening agent (from about 0.1% to about 3%), a coloring agent (from about 0.01% to about 0.5%), and the balance water. The compositions may comprise an anticaries agent (from about 0.05% to about 0.3% as fluoride ion), and an anticalculus agent (from about 0.1% to about 13%).

Preferred compositions of the subject invention may also be in the form of dentifrices, such as toothpastes, tooth gels and tooth powders. Components of such toothpaste and tooth gels generally include one or more of a dental abrasive (from about 6% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpaste or tooth gel may also include one or more of an anticaries agent (from about 0.05% to about 0.3% as fluoride ion), and an anticalculus agent (from about 0.1% to about 13%). Tooth powders, of course, contain substantially all non-liquid components.

Other preferred compositions of the subject invention are mouthwashes, including mouth sprays. Components of such mouthwashes and mouth sprays typically include one or more of water (from about 45% to about 95%), ethanol (from about 0% to about 25%), a humectant (from about 0% to about 50%), a surfactant (from about 0.01% to about 7%), a flavoring agent (from about 0.04% to about 2%), a sweetening agent (from about 0.1% to about 3%), and a coloring agent (from about 0.001% to about 0.5%). Such mouthwashes and mouth sprays may also include one or more of an anticaries agent (from about 0.05% to about 0.3% as fluoride ion), and an anticalculus agent (from about 0.1% to about 3%).

Other preferred compositions of the subject invention are dental solutions including irrigation fluids. Components of such dental solutions generally include one or more of water (from about 90% to about 99%), preservative (from about 0.01% to about 0.5%), thickening agent (from 0% to about 5%), flavoring agent (from about 0.04% to about 2%), sweetening agent (from about 0.1% to about 3%), and surfactant (from 0% to about 5%).

Chewing gum compositions typically include one or more of a gum base (from about 50% to about 99%), a flavoring agent (from about 0.4% to about 2%) and a sweetening agent (from about 0.01% to about 20%).

The term "lozenge" as used herein includes: breath mints, troches, pastilles, microcapsules, and fast-dissolving solid forms including freeze dried forms (cakes, wafers, thin films, tablets) and fast-dissolving solid forms including compressed tablets. The term "fast-dissolving solid form" as used herein means that the solid dosage form dissolves in less than about 60 seconds, preferably less than about 15 seconds, more preferably less than about 5 seconds, after placing the solid dosage form in the oral cavity. Fast-dissolving solid forms are disclosed in U.S. patent application Ser. No. 08/253,890, filed Jun. 3, 1994, Brideau; U.S. Pat. Nos. 4,642,903; 4,946,684; 4,305,502; 4,371,516; 5,188,825; 5,215,756; 5,298,261; 3,882, 228; 4,687,662; 4,642,903.

Lozenges include discoid-shaped solids comprising a therapeutic agent in a flavored base. The base may be a hard sugar candy, glycerinated gelatin or combination of sugar with sufficient mucilage to give it form. These dosage forms are generally described in Remington: The Science and Practice of Pharmacy, 19$^{th}$ Ed., Vol. 11, Chapter 92, 1995. Lozenge compositions (compressed tablet type) typically include one or more fillers (compressible sugar), flavoring agents, and lubricants. Microcapsules of the type contemplated herein are disclosed in U.S. Pat. No. 5,370,864, Peterson et al., issued Dec. 6, 1994.

In still another aspect, the invention comprises a dental implement impregnated with the present composition. The dental implement comprises an implement for contact with teeth and other tissues in the oral cavity, said implement being impregnated with a composition comprising the present copolymer of vinyl pyrrolidone with C2–C12 alkenyl esters of saturated C1–C19 alkyl carboxylic acids. The dental implement can be impregnated fibers including dental floss or tape, chips or strips and polymer fibers.

Types of carriers or oral care excipients which may be included in compositions of the present invention, along with specific non-limiting examples, are discussed in the following paragraphs.

Abrasives

Dental abrasives useful in the topical, oral carriers of the compositions of the subject invention include many different materials. The material selected must be one which is compatible within the composition of interest and does not excessively abrade dentin. Suitable abrasives include, for example, silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, and resinous abrasive materials such as particulate condensation products of urea and formaldehyde.

Another class of abrasives for use in the present compositions is the particulate thermo-setting polymerized resins as described in U.S. Pat. No. 3,070,510 issued to Cooley & Grabenstetter on Dec. 25, 1962. Suitable resins include, for example, melamines, phenolics, ureas, melamine-ureas, melamine-formaldehydes, urea-formaldehyde, melamine-urea-formaldehydes, cross-linked epoxides, and cross-linked polyesters.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975. Preferred are the silica xerogels marketed under the trade name "Syloid" by the W. R. Grace & Company, Davison Chemical Division. Also preferred are the precipitated silica materials such as those marketed by the J. M. Huber Corporation under the trade name, Zeodent®, particularly the silicas carrying the designation Zeodent® 119, Zeodent® 118, Zeodent® 109 and Zeodent® 129. The types of silica dental abrasives useful in the toothpastes of the present invention are described in more detail in Wason, U.S. Pat. No. 4,340,583, issued Jul. 29, 1982; and in commonly-assigned U.S. Pat. No. 5,603,920, issued on Feb. 18, 1997; U.S. Pat. No. 5,589,160, issued Dec. 31, 1996; U.S. Pat. No. 5,658,553, issued Aug. 19, 1997; U.S. Pat. No. 5,651,958, issued on Jul. 29, 1997, and U.S. Provisional Application Serial No. 60/300,766, filed Jun. 25, 2001.

Mixtures of abrasives can be used such as mixtures of the various grades of Zeodent® silica abrasives listed above. The total amount of abrasive in dentifrice compositions of the subject invention preferably range from about 6% to about 70% by weight; toothpastes preferably contain from about 10% to about 50% of abrasives, by weight of the composition. Solution, mouth spray, mouthwash and non-abrasive gel compositions of the subject invention typically contain no abrasive.

Surfactants

The present compositions may also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976. The present composition typically comprises an anionic surfactant at a level of from about 0.025% to about 9%, preferably from about 0.05% to about 5%, and most preferably from about 0.1% to about 1%.

Another preferred surfactant is one selected from the group consisting of sarcosinate surfactants, isethionate surfactants and taurate surfactants. Preferred for use herein are alkali metal or ammonium salts of these surfactants. Most preferred herein are the sodium and potassium salts of the following: lauroyl sarcosinate, myristoyl sarcosinate, palmitoyl sarcosinate, stearoyl sarcosinate and oleoyl sarcosinate. This surfactant can be present in the compositions of the present invention from about 0.1% to about 2.5%, preferably from about 0.3% to about 2.5% and most preferably from about 0.5% to about 2.0% by weight of the total composition.

Preferred cationic surfactants useful in the present invention can be broadly defined as derivatives of aliphatic quaternary ammonium compounds having one long alkyl chain containing from about 8 to 18 carbon atoms such as lauryl trimethylammonium chloride; cetyl pyridinium chloride; cetyl trimethylammonium bromide; di-isobutylphenoxyethyl-dimethylbenzylammonium chloride; coconut alkyltrimethylammonium nitrite; cetyl pyridinium fluoride; etc. Preferred compounds are the quaternary ammonium fluorides described in U.S. Pat. No. 3,535,421, Oct. 20, 1970, to Briner et al., where said quaternary ammonium fluorides have detergent properties. Certain cationic surfactants can also act as germicides in the compositions disclosed herein. Cationic surfactants such as chlorhexidine, although suitable for use in the current invention, are not preferred due to their capacity to stain the oral cavity's hard tissues. Persons skilled in the art are aware of this possibility and should incorporate cationic surfactants only with this limitation in mind.

Preferred nonionic surfactants that can be used in the compositions of the present invention can be broadly defined as compounds produced by the condensation of alkylene oxide groups (hydrophilic in nature) with an organic hydrophobic compound which may be aliphatic or alkylaromatic in nature. Examples of suitable nonionic surfactants include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

Preferred zwitterionic synthetic surfactants useful in the present invention can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate.

Preferred betaine surfactants are disclosed in U.S. Pat. No. 5,180,577 to Polefka et al., issued Jan. 19, 1993. Typical alkyl dimethyl betaines include decyl betaine or 2-(N-decyl-N,N-dimethylammonio) acetate, coco betaine or 2-(N-coc-N, N-dimethyl ammonio) acetate, myristyl betaine, palmityl betaine, lauryl betaine, cetyl betaine, cetyl betaine, stearyl betaine, etc. The amidobetaines are exemplified by cocoamidoethyl betaine, cocoamidopropyl betaine, lauramidopropyl betaine and the like. The betaines of choice are preferably the cocoamidopropyl betaine and, more preferably, the lauramidopropyl betaine.

Anticalculus Agent

The present compositions may also include an anticalculus agent, preferably a pyrophosphate ion source which is from a pyrophosphate salt. The pyrophosphate salts useful in the present compositions include the dialkali metal pyrophosphate salts, tetraalkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, preferably from about 1.5% to about 10%, and most preferably from about 2% to about 6%. Free pyrophosphate ions may be present in a variety of protonated states depending on a the pH of the composition.

Compositions comprising predominately undissolved pyrophosphate refer to compositions containing no more than about 20% of the total pyrophosphate salt dissolved in the composition, preferably less than about 10% of the total pyrophosphate dissolved in the composition. Tetrasodium pyrophosphate salt is the preferred pyrophosphate salt in these compositions. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, and is generally from about 1.5% to about 15%, preferably from about 2% to about 10%, and most preferably from about 3% to about 8%, by weight of the dentifrice composition.

Compositions may also comprise a mixture of dissolved and undissolved pyrophosphate salts. Any of the above mentioned pyrophosphate salts may be used.

The pyrophosphate salts are described in more detail in *Kirk-Othmer Encyclopedia of Chemical Technology*, Third Edition, Volume 17, Wiley-Interscience Publishers (1982).

Optional agents to be used in place of or in combination with the pyrophosphate salt include such known materials as synthetic anionic polymers, including polyacrylates and copolymers of maleic anhydride or acid and methyl vinyl ether (e.g., Gantrez), as described, for example, in U.S. Pat. No. 4,627,977, to Gaffar et al., as well as, e.g., polyamino propane sulfonic acid (AMPS), zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof.

Examples of phosphonate copolymers include the diphosphonate-derivatized polymers in U.S. Pat. No. 5,011,913 to Benedict et al. A preferred polymer is diphosphonate modified polyacrylic acid. Other suitable phosphonate-containing polymers are described in U.S. Pat. No. 5,980,776 to Zakikhani, et al.

Polyphosphates may also be included in the present compositions. A polyphosphate is generally understood to consist of two or more phosphate groups arranged primarily in a linear configuration, although some cyclic derivatives may be present. In addition to pyrophosphates and tripolyphosphate, which are technically polyphosphates, also desired are the polyphosphates having an average of about four or more phosphate groups, i.e., tetrapolyphosphate and hexametaphosphate, among others. Polyphosphates larger than tetrapolyphosphate usually occur as amorphous glassy materials, the linear "glassy" polyphosphates having the formula:

$$XO(XPO_3)_nX$$

wherein X is sodium or potassium and n averages from about 6 to about 125. Preferred polyphosphates are manufactured by FMC Corporation which are commercially known as Sodaphos (n≈6), Hexaphos (n≈13), and Glass H (n≈21). These polyphosphates may be used alone or in combination thereof.

Chelating Agents

Another preferred optional agent is a chelating agent such as tartaric acid and pharmaceutically-acceptable salts thereof, citric acid and alkali metal citrates and mixtures thereof. Chelating agents are able to complex calcium found in the cell walls of the bacteria. Chelating agents can also disrupt plaque by removing calcium from the calcium bridges which help hold this biomass intact. However, it is not desired to use a chelating agent which has an affinity for calcium that is too high, as this may result in tooth demineralization, which is contrary to the objects and intentions of the present invention.

Sodium and potassium citrate are the preferred alkali metal citrates, with sodium citrate being the most preferred. Also preferred is a citric acid/alkali metal citrate combination. Preferred herein are alkali metal salts of tartaric acid. Most preferred for use herein are disodium tartrate, dipotassium tartrate, sodium potassium tartrate, sodium hydrogen tartrate and potassium hydrogen tartrate. The amounts of chelating agent suitable for use in the present invention are about 0.1% to about 2.5%, preferably from about 0.5% to about 2.5% and more preferably from about 1.0% to about 2.5%. The tartaric acid salt chelating agent can be used alone or in combination with other optional chelating agents.

Other optional chelating agents can be used. Preferably these chelating agents have a calcium binding constant of about $10^1$ to $10^5$ provide improved cleaning with reduced plaque and calculus formation.

Still another possible group of chelating agents suitable for use in the present invention are the anionic polymeric polycarboxylates. Such materials are well known in the art, being employed in the form of their free acids or partially or preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez AN 139 (M.W. 500,000), AN 119 (M.W. 250,000) and preferably S-97 Pharmaceutical Grade (M.W. 70,000), of GAF Chemicals Corporation.

Other operative polymeric polycarboxylates include those such as the 1:1 copolymers of maleic anhydride with ethyl acrylate, hydroxyethyl methacrylate, N-vinyl-2-pyrrolidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates are disclosed in U.S. Pat. No. 4,138,477, Feb. 6, 1979 to Gaffar and U.S. Pat. No. 4,183,914, Jan. 15, 1980 to Gaffar et al. and include copolymers of maleic anhydride with styrene, isobutylene or ethyl vinyl ether; polyacrylic, polyitaconic and polymaleic acids; and sulfoacrylic oligomers of M.W. as low as 1,000 available as Uniroyal ND-2.

Fluoride Source

It is common to have an additional water-soluble fluoride compound present in dentifrices and other oral compositions in an amount sufficient to give a fluoride ion concentration in the composition at 25° C., and/or when it is used of from about 0.0025% to about 5.0% by weight, preferably from about 0.005% to about 2.0% by weight, to provide additional anticaries effectiveness. A wide variety of fluoride ion-yielding materials can be employed as sources of soluble fluoride in the present compositions. Examples of suitable fluoride ion-yielding materials are found in U.S. Pat. No. 3,535,421, Oct. 20, 1970 to Briner et al. and U.S. Pat. No. 3,678,154, Jul. 18, 1972 to Widder et al. Representative fluoride ion sources include: stannous fluoride, sodium fluoride, potassium fluoride, sodium monofluorophosphate and many others. Stannous fluoride and sodium fluoride are particularly preferred, as well as mixtures thereof.

Teeth Whitening Actives

Teeth whitening actives may be included in the oral care compositions of the present invention. The actives suitable for whitening include the peroxides, metal chlorites, perborates, percarbonates, peroxyacids, persulfates, and combinations thereof. Suitable peroxide compounds include hydrogen peroxide, urea peroxide, calcium peroxide, and mixtures thereof. Suitable metal chlorites include calcium chlorite, barium chlorite, magnesium chlorite, lithium chlorite, sodium chlorite, and potassium chlorite. The preferred chlorite is sodium chlorite. Additional whitening actives may be hypochlorite and chlorine dioxide. A preferred percarbonate is sodium percarbonate. Other suitable whitening agents include potassium, ammonium, sodium and lithium persulfates and perborate mono- and tetrahydrates, and sodium pyrophosphate peroxyhydrate.

Thickening Agents

In preparing toothpaste or gels, it is necessary to add some thickening material to provide a desirable consistency of the composition, to provide desirable active release characteristics upon use, to provide shelf stability, and to provide stability of the composition, etc. Preferred thickening agents are carboxyvinyl polymers, carrageenan, hydroxyethyl cellulose, laponite and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture.

A preferred class of thickening or gelling agents includes a class of homopolymers of acrylic acid crosslinked with an alkyl ether of pentaerythritol or an alkyl ether of sucrose, or carbomers. Carbomers are commercially available from B. F. Goodrich as the Carbopol® series. Particularly preferred Carbopols include Carbopol 934, 940, 941, 956, and mixtures thereof.

Copolymers of lactide and glycolide monomers, the copolymer having the molecular weight in the range of from about 1,000 to about 120,000 (number average), are useful for delivery of actives into the periodontal pockets or around the periodontal pockets as a "subgingival gel carrier." These polymers are described in U.S. Pat. Nos. 5,198,220, and 5,242,910, issued Mar. 30, 1993 and Sept. 7, 1993, respectively both to Damani, and U.S. Pat. No. 4,443,430, issued Apr. 17, 1984 to Mattei.

Thickening agents in an amount from about 0.1% to about 15%, preferably from about 2% to about 10%, more preferably from about 4% to about 8%, by weight of the total toothpaste or gel composition, can be used. Higher concentrations can be used for chewing gums, lozenges (including breath mints), sachets, non-abrasive gels and subgingival gels.

Humectants

Another optional component of the topical, oral carriers of the compositions of the subject invention is a humectant. The humectant serves to keep toothpaste compositions from hardening upon exposure to air, to give compositions a moist feel to the mouth, and, for particular humectants, to impart desirable sweetness of flavor to toothpaste compositions. The humectant, on a pure humectant basis, generally comprises from about 0% to about 70%, preferably from about 5% to about 25%, by weight of the compositions herein. Suitable humectants for use in compositions of the subject invention include edible polyhydric alcohols such as glycerin, sorbitol, xylitol, butylene glycol, polyethylene glycol, and propylene glycol, especially sorbitol and glycerin.

Flavoring and Sweetening Agents

Flavoring agents can also be added to the compositions. Suitable flavoring agents include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof. Flavoring agents are generally used in the compositions at levels of from about 0.001% to about 5%, by weight of the composition.

Sweetening agents which can be used include sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof. A composition preferably contains from about 0.1% to about 10% of these agents, preferably from about 0.1% to about 1%, by weight of the composition.

In addition to flavoring and sweetening agents, coolants, salivating agents, warming agents, and numbing agents can be used as optional ingredients in compositions of the present invention. These agents are present in the compositions at a level of from about 0.001% to about 10%, preferably from about 0.1% to about 1%, by weight of the composition.

The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred coolants are selected from the group consisting of menthol, 3-1-menthoxypropane-1,2-diol known as TK-10 manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979.

Preferred salivating agents of the present invention include Jambu® manufactured by Takasago. Preferred warming agents include capsicum and nicotinate esters, such as benzyl nicotinate. Preferred numbing agents include benzocaine, lidocaine, clove bud oil, and ethanol.

Alkali Metal Bicarbonate Salt

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The present composition may contain from about 0.5% to about 30%, preferably from about 0.5% to about 15%, and most preferably from about 0.5% to about 5% of an alkali metal bicarbonate salt.

Miscellaneous Carriers

Water employed in the preparation of commercially suitable oral compositions should preferably be of low ion content and free of organic impurities. Water generally comprises from about 5% to about 70%, and preferably from about 20% to about 50%, by weight of the aqueous compositions herein. These amounts of water include the free water which is added plus that which is introduced with other materials, such as with sorbitol.

Titanium dioxide may also be added to the present composition. Titanium dioxide is a white powder which adds opacity to the compositions. Titanium dioxide generally comprises from about 0.25% to about 5% by weight of the dentifrice compositions.

The pH of the present compositions is preferably adjusted through the use of buffering agents. Buffering agents, as used herein, refer to agents that can be used to adjust the pH of the compositions to a range of about pH 4.0 to about pH 10.0. Buffering agents include monosodium phosphate, trisodium phosphate, sodium hydroxide, sodium carbonate, sodium acid pyrophosphate, citric acid, and sodium citrate. Buffering agents can be administered at a level of from about 0.5% to about 10%, by weight of the present compositions.

Other optional agents that may be used in the present compositions include dimethicone copolyols selected from alkyl- and alkoxy-dimethicone copolyols, such as C12 to C20 alkyl dimethicone copolyols and mixtures thereof. Highly preferred is cetyl dimethicone copolyol marketed under the Trade Name Abil EM90. The dimethicone copolyol is generally present in a level of from about 0.01% to about 25%, preferably from about 0.1% to about 5%, more preferably from about 0.5% to about 1.5% by weight. The dimethicone copolyols aid in providing positive tooth feel benefits.

Other useful carriers include biphasic dentifrice formulations such as those disclosed in U.S. Pat. No. 5,213,790, issued May 23, 1993, U.S. Pat. No. 5,145,666, issued Sep. 8, 1992, and U.S. Pat. No. 5,281,410 issued Jan. 25, 1994 all to Lukacovic et al. and in U.S. Pat. Nos. 4,849,213 and 4,528,180 to Schaeffer.

Other Active Agents

The present invention may also include other agents, such as antimicrobial agents. Included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides. The water soluble antimicrobials include quaternary ammonium salts and bis-biquanide salts, among others. Triclosan monophosphate is an additional water soluble antimicrobial agent. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1, 3-bis(2-ethyl-hexyl)-5-methyl hexa hydropyrimidine, benzalkonium chloride, benzethonium chloride and methyl benzethonium chloride are exemplary of typical quaternary ammonium antibacterial agents. Other compounds are bis [4-(R-amino)-1-pyridinium] alkanes as disclosed in U.S. Pat. No. 4,206,215, issued Jun. 3, 1980, to Bailey. Other antimicrobials such as copper bisglycinate, copper glysinate, zinc citrate, and zinc lactate may also be included. Also useful are enzymes, including endoglycosidase, papain, dextranase, mutanase, and mixtures thereof. Such agents are disclosed in U.S. Pat. No. 2,946,725, Jul. 26, 1960, to Norris et al. and in U.S. Pat. No. 4,051,234, Sep. 27, 1977 to Gieske et al. Specific antimicrobial agents include chlorhexidine, triclosan, triclosan monophosphate, and flavor oils such as thymol. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al. These agents, which provide anti-plaque benefits, may be present at levels of from about 0.01% to about 5.0%, by weight of the dentifrice composition.

METHOD OF USE

The present invention also relates to methods for cleaning and polishing teeth and reducing the incidence of stain, plaque, gingivitis and calculus on dental enamel.

The method of use herein comprises contacting a subject's dental enamel surfaces and oral mucosa with the oral compositions according to the present invention. The method of use may be by brushing with a dentifrice, rinsing with a dentifrice slurry or mouthrinse, or chewing a gum product. Other methods include contacting the topical oral gel, mouthspray, or other form with the subject's teeth and oral mucosa. The subject may be any person or lower animal whose tooth surface contacts the oral composition.

It should be understood that the present invention relates not only to methods for delivering the present compositions to the oral cavity of a human, but also to methods of delivering these compositions to the oral cavity of other animals, e.g., household pets or other domestic animals, or animals kept in captivity.

For example, a method of use may include brushing a dog's teeth with one of the dentifrice compositions. Another example would include the rinsing of a cat's mouth with an oral composition for a sufficient amount of time to see a benefit. Pet care products such as chews and toys may be formulated to contain the present oral compositions. The composition including the present copolymer is incorporated into a relatively supple but strong and durable material such as rawhide, ropes made from natural or synthetic fibers, and polymeric articles made from nylon, polyester or thermoplastic polyurethane. As the animal chews, licks or gnaws the product, the incorporated active elements are released into the animal's oral cavity into a salivary medium, comparable to an effective brushing or rinsing.

EXAMPLES

The following examples further describe and demonstrate embodiments within the scope of the present invention. These examples are given solely for the purpose of illustration and are not to be construed as limitations of the present invention as many variations thereof are possible without departing from the spirit and scope.

Example I

Evaluation of Whitening Performance

The whitening performance of oral solutions according to the present invention are compared with a treatment solution containing only tripolyphosphate. Results demonstrate enhanced whitening performance when the present copolymer is used in combination with tripolyphosphate as measured by changes in $L^*$, $b^*$ and E values.

Saliva coated HAP powder was stained with tea and exposed to one minute rinse with test solutions. Change in stain on the powders was determined from the changes in $L^*$ and $b^*$ values. These values are derived using the International Commission of Illumination (CIE) standard expressed as $L^*$, $a^*$, $b^*$, a numerical expression of three dimensional color space where $L^*$ represents lightness on the y axis, $a^*$ represents chroma (red-green) on the x axis, and $b^*$ represents chroma (yellow-blue) on the z axis. Delta E is the square root of the sum of the square of the differences for each expression. The changes in $L^*$ and $b^*$, which are significant for the present testing, were determined photometrically.

| Treatment | Change in L | Change in b | Change in E |
|---|---|---|---|
| 5% Tripolyphosphate (TPP) | 7.36 | −10.82 | 13.30 |
| 5% 60/40 PVP/VA | 2.17 | 0.15 | 2.27 |
| 5% TPP + 5% 60/40 PVP/VA | 15.15 | −14.33 | 21.25 |

Example II

Effect of Brushing with Toothpaste Formulations

Bovine chips stained with a stain mixture containing coffee, tea, iron, and bacteria were brushed with slurry of the following toothpastes for 200 strokes. Change in $L^*$ was determined using digital imaging. Results demonstrate enhanced whitening and stain removal with the current invention compared to commercial products.

| Treatment | Change in L* | Change in E |
|---|---|---|
| Fluoride Toothpaste | 1.88 | 1.91 |
| Tartar Control Toothpaste | 9.31 | 9.71 |
| PVP/VA + TPP Toothpaste | 13.63 | 13.79 |

Example III

Polishing Effect of Formulations Containing Silica Abrasive

The polishing effect of the formulations is determined according to an enamel polishing index, developed in our laboratories as described in commonly assigned U.S. Provisional Application Serial No. 60/300,766, filed Jun. 25, 2001. The % reduction in roughness of bovine enamel surfaces are measured following brushing with slurries of test dentifrice formulations. Results demonstrate that higher reduction in surface roughness are obtained with the formulations containing the present copolymer and abrasive compared to formulations containing abrasive alone.

| Treatment | % Reduction in Roughness |
|---|---|
| 25% Zeodent 119 slurry | 17.02 |
| 25% Zeodent 119 + PVP/VA slurry | 23.99 |
| 25% Zeodent 109 slurry | 35.98 |
| 25% Zeodent 109 + PVP/VA slurry | 40.10 |

Example IV

Dentifrice Formulations

Dentifrice compositions according to the present invention with different levels of copolymer, tripolyphosphate, silica abrasive and bleaching agent are shown below. These compositions are made using conventional methods.

| Component | IVA Wt % | IVB Wt % | IVC Wt % | IVD Wt % | IVE Wt % | IVF Wt % |
|---|---|---|---|---|---|---|
| Sorbitol Solution (70%) | 24.0 | 30.0 | 24.0 | 24.0 | 26.0 | 30.0 |
| Silica-Zeodent 109 | — | — | 15.0 | 12.5 | — | — |
| Silica-Zeodent 118 | 15.0 | — | 15.0 | — | 15.0 | 20.0 |
| Silica-Zeodent 119 | 15.0 | — | — | 12.5 | 15.0 | — |
| Tetrasodium Pyrophosphate | — | — | — | — | 5.0 | — |
| Sodium Tripolyphosphate | — | 5.0 | 5.0 | 3.0 | — | 3.0 |
| 60/40 PVP/VA | 5.0 | 3.0 | 5.0 | 1.0 | 3.0 | — |
| 70/30 PVP/VA | — | — | — | — | 2.0 | — |
| Thickening Silica | — | 6.0 | 1.0 | 1.0 | — | 1.0 |
| Glycerin | 8.0 | 12.0 | 8.0 | 8.0 | 6.0 | 10.0 |
| Polyethylene Glycol 300, NF (PEG-6) | — | 6.0 | — | 6.0 | — | — |
| Sodium Alkyl Solution (27.9%) | 5.0 | 5.0 | 5.0 | 5.0 | 5.0 | 5.0 |
| Sodium Bicarbonate | 1.5 | 1.5 | — | — | 1.5 | 1.5 |
| Poloxamer 407, NF | 1.5 | 1.25 | 1.25 | 1.25 | — | 1.5 |
| Flavor | 1.1 | 0.6 | 1.1 | 1.1 | 1.1 | 1.0 |
| Titanium Dioxide/Carnauba Wax Prills | — | 1.0 | 1.0 | — | 1.0 | 1.0 |
| Sodium Carboxymethyl Cellulose | 0.8 | 0.8 | 0.75 | 0.75 | 0.75 | |
| Xanthan Gum | — | 0.5 | 0.5 | — | — | — |
| Carbopol 956 | — | 0.4 | 0.4 | — | — | — |
| Sodium Saccharin | 0.35 | 0.35 | 0.35 | 0.35 | 0.35 | 0.35 |
| Sodium Carbonate | 0.5 | 0.5 | — | — | 0.5 | 0.5 |
| Sodium Phosphate | — | 0.5 | 0.5 | — | — | — |
| Trisodium Phosphate | — | 1.5 | 1.5 | — | — | — |
| Sodium Fluoride | 0.243 | 0.243 | 0.243 | 0.243 | 0.243 | 0.243 |
| Color | — | 0.05 | 0.05 | 0.05 | 0.05 | 0.05 |
| Water, Purified USP | QS | QS | QS | QS | QS | QS |

| Component | IV G Wt % | IV H Wt % | IV J Wt % | IV K Wt % | IV M Part A Wt % | IV M Part B Wt. % |
|---|---|---|---|---|---|---|
| Sorbitol Solution (70%) | — | — | — | — | 48.0 | — |
| Precipitated Silica | 30.0 | 25.0 | 30 | 20 | 26.0 | — |
| Sodium Tripolyphosphate | 5.0 | — | — | — | 3.5 | — |
| 60/40 PVP/VA | 5.0 | 5.0 | 5.0 | — | 3.0 | — |
| 70/30 PVP/VA | — | — | — | 7.0 | — | — |
| Thickening Silica | 1.0 | 1.0 | 1.0 | 1.0 | — | — |
| Sodium Alkyl Solution (27%) | — | — | — | — | 5.0 | — |
| Poloxomer 407, NF | 1.25 | 1.25 | 1.25 | 1.25 | — | — |
| Flavor | 1.1 | 1.1 | 1.1 | 1.1 | 0.8 | — |
| Titanium Dioxide/Carnauba Wax Prills | 1.0 | 1.0 | 1.0 | 1.0 | 0.5 | — |
| Sodium Carboxymethyl Cellulose | — | — | — | — | 0.6 | — |
| Xanthan Gum | 0.5 | 0.5 | 0.5 | 0.5 | 0.5 | — |
| Carbopol 956 | 0.4 | 0.4 | 0.4 | 0.4 | | — |
| Sodium Saccharin | 0.35 | 0.35 | 0.35 | 0.35 | 0.4 | — |
| Sodium Phosphate | 0.5 | 0.5 | 0.5 | 0.5 | | — |
| Trisodium Phosphate | 1.5 | 1.5 | 1.5 | 1.5 | 1.5 | — |
| Sodium Fluoride | 0.243 | 0.243 | 0.243 | 0.243 | 0.243 | — |
| Urea Peroxide | 5.5 | 5.5 | 10.0 | 10.0 | — | 15.0 |
| Carboxypolymethylene | | | | | | 5.0 |
| Glycerin | QS | QS | QS | QS | — | 70.0 |
| Water, Purified USP and Minors[1] | — | — | — | — | QS | QS |

[1]E.g., NaOH to adjust pH.

Example V

Mouthrinse

| Ingredient | Weight % |
|---|---|
| Water | 24.000 |
| Propylene Glycol | 53.459 |
| Sodium Tripolyphosphate | 5.000 |
| Sodium Benzoate | 0.320 |
| Benzoic Acid | 0.021 |
| Sodium Saccharin | 0.700 |
| 60/40 PVP/VA | 5.000 |
| Poloxamer 407 | 10.000 |
| Flavor | 1.500 |

Example V is prepared as follows: Mix water, poloxamer and propylene glycol. Next add the flavor, benzoic acid, tripolyphosphate and PVP/VA. Finally add the sodium benzoate and sodium saccharin and mix until homogeneous.

Example VI

Tooth Gel

Example VI illustrates aqueous and non-aqueous tooth gel compositions prepared by mixing the liquid carriers, next adding the saccharin, sodium tripolyphosphate and PVP/VA and mixing until homogeneous.

| Component | VIA Wt. % | VIB Wt. % |
|---|---|---|
| 60/40 PVP/VA | 5.0 | 5.0 |
| Sodium Tripolyphosphate | 2.0 | 2.0 |
| Sodium Saccharin | 0.5 | 0.5 |
| Urea Peroxide | — | 15.0 |
| Ethanol | 32.5 | — |
| Water | 60.0 | — |
| Glycerin | — | 35.0 |
| PEG | — | 42.5 |

Example VII

Chewing Gum

Chewing gum compositions including a coated chewing gum (VIIC) according to the present invention are shown below.

| Component | VIIA | VIIB |
|---|---|---|
| Xylitol | 16.700 | 16.700 |
| Gum base (e.g., Prestige-PL, Cafosa) | 28.000 | 28.000 |
| 60/40 PVP/VA | 5.000 | 3.000 |
| Sodium tripolyphosphate | 5.000 | 7.000 |
| Hydrogenated starch hydrolysate (85% solids) | 8.000 | 8.000 |
| Glycerin | 7.000 | 7.000 |
| Mannitol | 5.000 | 5.000 |
| Flavor | 1.600 | 1.600 |
| Aspartame | 0.200 | 0.200 |
| Spray dried menthol | 0.150 | 0.150 |
| Sorbitol | QS | QS |

Making Instructions

Example VIIA and VIIB

Heat gum base to −45° C. to soften. Maintain mixer vessel cavity at −45° C. during entire mixing process. Add gum base to mixing cavity of double sigma blade mixer and mix for 5 minutes. Add mannitol and spray-dried menthol. Mix for 2 minutes. Add 50% of sorbitol and mix for 2 minutes. Add glycerin and mix for 2 minutes. Add 50% of xylitol and mix for 2 minutes. Add hydrogenated starch hydrolysate and mix for 5 minutes. Add second 50% sorbitol and mix for 3 minutes. Add second 50% of xylitol, PVP/VA, sodium tripolyphosphate and aspartame and mix for 3 minutes. Add flavor and mix for 3 minutes.

| VIIC Component | Core % w/w 1 g/piece | Coating % w/w 0.35 g/piece | Total % w/w 1.35 g/piece |
|---|---|---|---|
| Sorbitol | 49.35 | — | 36.56 |
| Gum base[1] | 25.0 | — | 18.52 |
| PVP/VA 60/40 | 5.0 | | 3.70 |
| Sodium tripolyphosphate | 5.0 | — | 3.70 |
| Sodium fluoride | — | 0.08 | 0.02 |
| Hydrogenated Starch Hydrolysate | 5.0 | — | 3.70 |
| Mannitol | 2.0 | — | 1.48 |
| Glycerin | 5.0 | — | 3.70 |
| Titanium dioxide | — | 2.0 | 0.52 |
| Flavor | 2.0 | 2.0 | 2.00 |
| Additional spray-dried flavor | 1.5 | — | 1.11 |
| Sucralose | 0.05 | 0.03 | 0.05 |
| Potassium Acesulfame | 0.10 | 0.10 | 0.10 |
| Sorbitol[2] | — | 95.25 | 24.70 |
| Polysorbate 60 | — | 0.30 | 0.08 |
| Insoluble edible glitter[3] (Brilliant Blue) | — | 0.04 | 0.01 |
| Wax[4] | — | 0.20 | 0.05 |
| TOTAL | 100.00 | 100.00 | 100.00 |

[1]Comprises several ingredients, including pre-supplied gum bases from suppliers such as L. A. Dreyfus Company, 3775 Park Avenue, Edison, N. Jersey, US; Cafosa Gum, Calabria 267, 08029, Barcelona, Spain, etc.
[2]Level of Sorbitol refers to absolute level after drying; Sorbitol is added as a 70% aqueous solution
[3]Watson Foods Company Incorporated, 301 Heffernan Drive, West Haven, Connecticut, USA
[4]Level of wax refers to absolute level after drying wax is added as a 28% ethanolic solution; wax used comprises several ingredients such as that supplied by Kaul GmBH, Elmshorn, Germany Making Instructions Core Formulation Soften gum base with gentle heating and add mannitol, spray-dried flavor, glycerin, 50% of xylitol, hydrogenated starch hydrolysate, 50% of sorbitol and mix thoroughly. Add Add second 50% of sorbitol and mix for 2 minutes. Add second 50% of xylitol, sodium tripolyphosphate, PVP/VA and aspartame, remainder of flavor and mix further. Form bulk chewing gum mass into discrete pieces of desired shape and size using rolling and scoring equipment.

Coating Solution

Add titanium dioxide and Polysorbate 60 to 70% aqueous sorbitol solution and mix. Add flavor followed by Sucralose and Potassium Acesulfame and mix further.

Coating of Core Formulation

Place gum pieces into a coating pan and apply coating solution, partially dry. Repeat coating step until desired coating thickness or weight is achieved. Apply clear 70% aqueous sorbitol solution and, whilst wet, dry spray speckles onto product surface, dry. Apply second coat of clear 70% sorbitol solution followed by wax coating and allow product to fully dry.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. An oral care composition comprising an orally acceptable carrier, at least about 0.1% by weight of a water-soluble or water-dispersible copolymer comprised of one or a mixture of vinyl pyrrolidone (VP) monomeric units and one or a mixture of C2–C12 alkenyl C1–C19 saturated alkyl carboxylate (AC) monomeric units, and one or a mixture of oral care agents selected from the group consisting of polyphosphates having a chain length of at least about 3, abrasive polishing agents, and teeth bleaching actives,
   wherein said oral care compositions is in a form selected from toothpaste, dentifrice, tooth powder, topical oral gel, mouthrinse, denture product, mouthspray, lozenge, oral tablet, chewing gum and impregnated dental implement and wherein said composition provides enhanced cleaning, whitening and stain removal from teeth.

2. An oral care composition according to claim 1 wherein the copolymer is prepared by copolymerizing one or a mixture of vinyl pyrrolidone (VP) monomers with one or a mixture of C1–C19 saturated alkyl carboxylic acid (AC) C2–C12 alkenyl ester monomers, as follows:

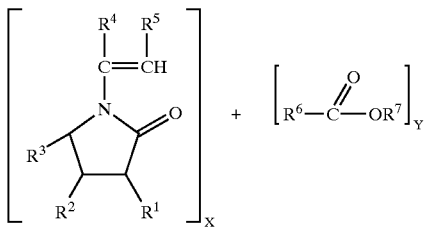

wherein $R^1$, $R^2$, $R^3$, $R^4$, $R^5$, =H or saturated C1–C12 alkyl. $R^6$=saturated straight- or branched-chain C1–C19 alkyl; $R^7$=C2–C12 alkenyl, and x/y weight ratio ranges from about 30/70 to about 90/10.

3. An oral care composition according to claim 2, wherein the copolymer is selected from copolymers of vinyl pyrrolidone with one or a mixture of vinyl acetate, vinyl propionate, or vinyl butyrate.

4. An oral care composition according to claim 3 comprising from about 0.1% to about 20.0% of a tooth bleaching agent selected from peroxides, metal chlorites, perborates, percarbonates, peroxyacids, persulfates, and combinations thereof.

5. An oral care composition comprising
(a) at least about 0.1% by weight of a water-soluble or water-dispersible copolymer comprised of one or a mixture of vinyl pyrrolidone (VP) monomeric units and one or a mixture of C2–C12 alkenyl C1–C19 saturated alkyl carboxylate (AC) monomeric units,
(b) at least about 0.5% by weight of a water soluble tripolyphosphate salt, and
(c) an orally acceptable carrier,
wherein said oral care compositions is in a form selected from toothpaste, dentifrice, tooth powder, topical oral gel, mouthrinse, denture product mouthspray, lozenge, oral tablet, chewing gum and impregnated dental implement and wherein said composition provides enhanced cleaning, whitening and stain removal from teeth.

6. An oral care composition according to claim 5 wherein the water-soluble or water-dispersible copolymer is selected from copolymers of vinyl pyrrolidone with one or a mixture of vinyl acetate, vinyl propionate, or vinyl butyrate and wherein the tripolyphosphate salt is selected from the group consisting of an alkali metal tripolyphosphate, ammonium tripolyphosphate and mixtures thereof.

7. An oral care composition according to claim 6 comprising from about 0.5% to about 100% vinyl pyrrolidone/vinyl acetate copolymer and from about 2.0% to about 20.0% tripolyphosphate salt.

8. An oral care composition according to claim 7 further comprising from about 0.1% to about 20.0% bleaching agent selected from peroxides, metal chlorites, perborates, percarbonates peroxyacids, persulfates, and combinations thereof.

9. An oral care composition comprising
(a) at least about 0.1% by weight of a water-soluble or water-dispersible copolymer prepared by copolymerizing one or a mixture of vinyl pyrrolidone (VP) monomeric units and one or a mixture of C2–C12 alkenyl C1–C19 saturated alkyl carboxylate (AC) monomeric units,
(b) at least about 6% by weight of an abrasive polishing agent, and
(c) an orally acceptable carrier,
wherein said oral care compositions is in a form selected from toothpaste, dentifrice, tooth powder, topical oral gel, mouthrinse, denture product, mouthspray, lozenge, oral tablet, chewing gum and impregnated dental implement and wherein said composition provides enhanced cleaning, whitening, polishing and stain removal from teeth.

10. An oral care composition according to claim 9, wherein the water-soluble or water-dispersible copolymer is selected from copolymers of vinyl pyrrolidone with one or a mixture of vinyl acetate, vinyl propionate, or vinyl butyrate and wherein the polishing agent comprises one or a mixture of silica abrasives.

11. An oral care composition according to claim 10 comprising from about 0.5% to about 10.0% vinyl pyrrolidone/vinyl acetate copolymer and from about 6% to about 70% silica abrasive by weight of the composition.

12. An oral care composition according to claim 11 further comprising from about 2.0% to about 20.0% by weight of a tripolyphosphate salt selected from the group consisting of an alkali metal tripolyphosphate, ammonium tripolyphosphate and mixtures thereof.

13. An oral care composition according to claim 12 further comprising from about 0.1% to about 20.0% bleaching agent selected from peroxides, metal chlorites, perborates, percarbonates, peroxyacids, persulfates, and combinations thereof.

14. An oral care composition according to claim 13, wherein the bleaching agent is selected from the group consisting of hydrogen peroxide, urea peroxide, calcium peroxide, sodium percarbonate and mixtures thereof.

15. A method for overall cleaning and whitening of teeth and for removing and preventing surface deposited stains on teeth comprising contacting a subject's teeth with an oral composition according to claim 1.

16. A method for overall cleaning and whitening of teeth and for removing and preventing surface deposited stains on teeth comprising contacting a subject's teeth with an oral composition according to claim 5.

17. A method for overall cleaning, whitening and polishing of teeth and for removing and preventing surface deposited stains on teeth comprising contacting a subject's teeth with an oral composition according to claim 9.

* * * * *